(12) United States Patent
Opara

(10) Patent No.: US 6,783,964 B2
(45) Date of Patent: Aug. 31, 2004

(54) MICROENCAPSULATED PANCREATIC ISLET CELLS

(75) Inventor: Emmanuel C. Opara, Durham, NC (US)

(73) Assignee: Duke University, Durham, NC (US)

( * ) Notice: Subject to any disclaimer, the term of this patent is extended or adjusted under 35 U.S.C. 154(b) by 100 days.

(21) Appl. No.: 10/054,796

(22) Filed: Jan. 23, 2002

(65) Prior Publication Data

US 2002/0098559 A1 Jul. 25, 2002

Related U.S. Application Data

(60) Division of application No. 09/453,348, filed on Dec. 1, 1999, now Pat. No. 6,365,385, which is a continuation-in-part of application No. 09/273,407, filed on Mar. 22, 1999, now Pat. No. 6,303,355.

(51) Int. Cl.[7] .......................... C12N 11/10; C12N 11/04; C12N 5/02; C12N 5/06; A61K 35/12

(52) U.S. Cl. ...................... 435/178; 424/93.7; 424/423; 424/489; 435/182; 435/375; 435/382; 435/384; 435/395; 435/404

(58) Field of Search ................................ 435/178, 182, 435/375, 382, 384, 395, 404; 424/93.7, 423, 489

(56) References Cited

U.S. PATENT DOCUMENTS

| | | | |
|---|---|---|---|
| 4,237,229 A | 12/1980 | Hartdegen et al. | 435/182 |
| 4,298,002 A | 11/1981 | Ronel et al. | 128/260 |
| 4,323,457 A | 4/1982 | Sun et al. | 210/645 |
| 4,352,883 A | 10/1982 | Lim | 435/178 |
| 4,353,888 A | 10/1982 | Sefton | 424/25 |
| 4,378,016 A | 3/1983 | Loeb | 128/260 |
| 4,386,895 A | 6/1983 | Sodickson | 425/5 |
| 4,391,909 A | 7/1983 | Lim | 435/178 |
| 4,402,694 A | 9/1983 | Ash et al. | 604/891 |
| 4,407,957 A | 10/1983 | Lim | 435/178 |
| 4,409,331 A | 10/1983 | Lim | 435/178 |
| 4,439,521 A | 3/1984 | Archer et al. | 435/1 |
| 4,459,252 A | 7/1984 | MacGregor | 264/46.9 |
| 4,485,096 A | 11/1984 | Bell | 424/95 |
| 4,495,288 A | 1/1985 | Jarvis, Jr. et al. | 435/241 |
| 4,539,716 A | 9/1985 | Bell | 623/1 |
| 4,546,500 A | 10/1985 | Bell | 623/1 |
| 4,550,022 A | 10/1985 | Garabedian et al. | 424/127 |
| 4,582,799 A | 4/1986 | Jarvis, Jr. | 435/68 |
| 4,627,836 A | 12/1986 | MacGregor | 604/93 |
| 4,663,286 A | 5/1987 | Tsang et al. | 435/178 |
| 4,673,566 A | 6/1987 | Goosen et al. | 424/19 |
| 4,681,839 A | 7/1987 | Swartz | 435/1 |
| 4,689,293 A | 8/1987 | Goosen et al. | 435/1 |
| 4,692,284 A | 9/1987 | Braden | 264/4.3 |
| 4,733,336 A | 3/1988 | Skogler et al. | 362/142 |
| 4,744,515 A | 5/1988 | Watanabe | 239/70 |
| 4,778,749 A | 10/1988 | Vasington et al. | 435/2 |
| 4,789,550 A | 12/1988 | Hommel et al. | 424/493 |
| 4,798,786 A | 1/1989 | Tice et al. | 435/177 |
| 4,798,824 A | 1/1989 | Belzer et al. | 514/60 |
| 4,803,168 A | 2/1989 | Jarvis, Jr. | 435/240.22 |
| 4,806,355 A | 2/1989 | Goosen et al. | 424/424 |
| 4,814,274 A | 3/1989 | Shioya et al. | 435/174 |
| 4,822,534 A | 4/1989 | Lencki et al. | 264/4.3 |
| 4,829,087 A | 5/1989 | Ammon | 514/562 |
| 4,837,021 A | 6/1989 | Andermann et al. | 424/602 |
| 4,861,704 A | 8/1989 | Reemtsma et al. | 435/1 |
| 4,870,002 A | 9/1989 | Kiel | 435/2 |
| 4,879,283 A | 11/1989 | Belzer et al. | 514/60 |
| 4,902,295 A | 2/1990 | Walthall et al. | 623/11 |
| 4,911,717 A | 3/1990 | Gaskill, III | 623/11 |
| 4,927,761 A | 5/1990 | Reading et al. | 435/178 |
| 4,935,000 A | 6/1990 | Dudek | 600/36 |
| 4,936,317 A | 6/1990 | MacGregor | 128/784 |
| 4,938,961 A | 7/1990 | Collins et al. | 424/606 |
| 4,942,129 A | 7/1990 | Goosen et al. | 435/182 |
| 4,946,438 A | 8/1990 | Reemtsma et al. | 604/53 |
| 4,956,128 A | 9/1990 | Hommel et al. | 264/4 |
| 4,969,286 A | 11/1990 | Belanger | 43/25 |
| 4,997,443 A | 3/1991 | Walthall et al. | 623/11 |
| 5,002,661 A | 3/1991 | Chick et al. | 210/192 |
| 5,015,476 A | 5/1991 | Cochrum et al. | 424/423 |
| 5,032,398 A | 7/1991 | Kaslow | 424/92 |
| 5,040,960 A | 8/1991 | Shioya et al. | 425/5 |
| 5,066,578 A | 11/1991 | Wikman-Coffelt | 435/1 |
| 5,071,741 A | 12/1991 | Brockbank | 435/1 |
| 5,073,491 A | 12/1991 | Familletti | 435/240.22 |
| 5,082,831 A | 1/1992 | Leaf et al. | 514/56 |
| 5,084,350 A | 1/1992 | Chang et al. | 428/402.2 |

(List continued on next page.)

FOREIGN PATENT DOCUMENTS

| | | | |
|---|---|---|---|
| EP | 0188309 | 5/1990 | A61K/9/50 |
| WO | WO91/09119 | 6/1991 | C12N/11/10 |
| WO | WO93/09176 | 5/1993 | C08L/1/00 |
| WO | WO94/08570 | 4/1994 | A61K/9/50 |
| WO | WO97/30778 | 8/1997 | B01D/63/06 |

OTHER PUBLICATIONS

Bartlett et al.; Prevention of Recurrent Autoimmune Islet Transplant Destruction by Simultaneous Kidney Transplantation, *Transplantation Proceedings*, 26:2 737 (1994).

Brunicardi et al.; Issues in Clinical Islet Transplantation, *Pancreas*, 9:3 281–290 (1994).

Lim et al.; Microencapsulated Islets as Bioartificial Endocrine Pancreas, *Science*, 210 908–910 (1980).

(List continued on next page.)

*Primary Examiner*—David M. Naff
(74) *Attorney, Agent, or Firm*—Myers Bigel Sibley & Sajovec

(57) ABSTRACT

Methods of treating and forming biocompatible microcapsules that contain living cells are provided, to improve the function of the microcapsules. In particular, methods of treating islet cells or microcapsules containing islet cells are provided. Culture of isolated islet cells prior to encapsulation, culture of encapsulated cells, and cryopreservation of islet cells prior to encapsulation, are described. Methods for harvesting viable islets that incorporates an anti-oxidant in the digestion medium are also disclosed.

12 Claims, 6 Drawing Sheets

U.S. PATENT DOCUMENTS

| | | |
|---|---|---|
| 5,110,722 A | 5/1992 | Brockbank et al. ............. 435/1 |
| 5,116,493 A | 5/1992 | Chick et al. ................ 210/192 |
| 5,116,494 A | 5/1992 | Chick et al. ................ 210/192 |
| 5,131,907 A | 7/1992 | Williams et al. .............. 600/36 |
| 5,135,915 A | 8/1992 | Czarniecki et al. ........... 514/21 |
| 5,145,771 A | 9/1992 | Lemasters et al. ............. 435/1 |
| 5,149,543 A | 9/1992 | Cohen et al. ............... 424/499 |
| 5,158,881 A | 10/1992 | Aebischer et al. .......... 435/182 |
| 5,171,660 A | 12/1992 | Carpenter et al. ............. 435/1 |
| 5,175,004 A | 12/1992 | Matsumura ................ 424/520 |
| 5,175,093 A | 12/1992 | Seifert ........................ 435/41 |
| 5,200,176 A | 4/1993 | Wong et al. ............... 424/85.1 |
| 5,200,398 A | 4/1993 | Strasberg et al. ............. 514/23 |
| 5,222,982 A | 6/1993 | Ommaya ..................... 623/12 |
| 5,227,298 A | 7/1993 | Weber et al. ............... 435/178 |
| 5,232,848 A | 8/1993 | Wolfe et al. ........... 435/240.31 |
| 5,260,002 A | 11/1993 | Wang ........................ 264/4.1 |
| 5,273,904 A | 12/1993 | Langley ...................... 435/287 |
| 5,283,058 A | 2/1994 | Faustman ..................... 424/88 |
| 5,284,761 A | 2/1994 | Aebischer et al. .......... 435/182 |
| 5,286,495 A | 2/1994 | Batich et al. ............... 424/490 |
| 5,306,711 A | 4/1994 | Andrews ..................... 514/59 |
| 5,308,701 A | 5/1994 | Cohen et al. .......... 428/402.22 |
| 5,314,471 A | 5/1994 | Brauker et al. ............... 623/11 |
| 5,314,814 A | 5/1994 | Harder et al. ............... 435/177 |
| 5,322,790 A | 6/1994 | Scharp et al. ............... 435/268 |
| 5,324,518 A | 6/1994 | Orth et al. .................. 424/423 |
| 5,328,821 A | 7/1994 | Fisher et al. ................... 435/1 |
| 5,334,640 A | 8/1994 | Desai et al. ................. 524/56 |
| 5,344,454 A | 9/1994 | Clarke et al. ................. 623/1 |
| 5,364,756 A | 11/1994 | Livesey et al. ................ 435/2 |
| 5,370,681 A | 12/1994 | Herweck et al. .............. 623/1 |
| 5,370,870 A | 12/1994 | Wong ....................... 424/85.1 |
| 5,370,989 A | 12/1994 | Stern et al. .................... 435/1 |
| 5,376,542 A | 12/1994 | Schlegal .................. 435/172.2 |
| 5,380,536 A | 1/1995 | Hubbell et al. .............. 424/497 |
| 5,387,237 A | 2/1995 | Fournier et al. ............... 623/11 |
| 5,389,535 A | 2/1995 | Aebischer et al. .......... 435/182 |
| 5,395,314 A | 3/1995 | Klatz et al. .................. 604/24 |
| 5,399,665 A | 3/1995 | Barrera et al. .............. 528/354 |
| 5,403,834 A | 4/1995 | Malfroy-Camine et al. . 514/185 |
| 5,405,742 A | 4/1995 | Taylor ........................... 435/1 |
| 5,410,016 A | 4/1995 | Hubbell et al. .............. 528/354 |
| 5,418,154 A | 5/1995 | Aebischer et al. .......... 435/182 |
| 5,424,207 A | 6/1995 | Carpenter et al. ........... 435/260 |
| 5,425,764 A | 6/1995 | Fournier et al. ............... 623/11 |
| 5,427,935 A | 6/1995 | Wang et al. ................. 435/178 |
| 5,427,940 A | 6/1995 | Newgard ................. 435/240.2 |
| 5,429,821 A | 7/1995 | Dorian et al. ............... 424/424 |
| 5,443,950 A | 8/1995 | Naughton et al. ............. 435/1 |
| 5,447,863 A | 9/1995 | Langley ...................... 435/268 |
| 5,453,270 A | 9/1995 | Bills ......................... 424/93.7 |
| 5,453,278 A | 9/1995 | Chan et al. ................. 424/422 |
| 5,453,368 A | 9/1995 | Tresco et al. ................ 435/182 |
| 5,459,054 A | 10/1995 | Skjak-Braek et al. ........ 435/178 |
| 5,462,866 A | 10/1995 | Wang ......................... 435/174 |
| 5,470,731 A | 11/1995 | Cochrum ................... 435/178 |
| 5,487,739 A | 1/1996 | Aebischer et al. ........ 604/890.1 |
| 5,494,682 A | 2/1996 | Cohen et al. ............... 424/489 |
| 5,496,722 A | 3/1996 | Goodwin et al. ....... 435/240.23 |
| 5,498,427 A | 3/1996 | Menasche .................. 424/678 |
| 5,510,263 A | 4/1996 | Quaranta et al. ...... 435/240.243 |
| 5,514,377 A | 5/1996 | Cochrum et al. ........... 424/423 |
| 5,514,378 A | 5/1996 | Mikos et al. ............... 424/425 |
| 5,514,536 A | 5/1996 | Taylor ........................ 435/1.2 |
| 5,516,681 A | 5/1996 | Naughton et al. ..... 435/240.243 |
| 5,521,079 A | 5/1996 | Dorian et al. ............... 435/174 |
| 5,529,066 A | 6/1996 | Palti ........................... 128/635 |
| 5,529,914 A | 6/1996 | Hubbell et al. .............. 435/182 |
| 5,531,997 A | 7/1996 | Cochrum .................... 424/424 |
| 5,534,025 A | 7/1996 | Moussy ....................... 623/11 |
| 5,534,404 A | 7/1996 | Laurance et al. ............... 435/3 |
| 5,545,222 A | 8/1996 | Bonutti ....................... 623/11 |
| 5,545,223 A | 8/1996 | Neuenfeldt et al. ........... 623/11 |
| 5,547,724 A | 8/1996 | Kuribayashi ............... 428/35.8 |
| 5,549,675 A | 8/1996 | Neuenfeldt et al. ........... 623/11 |
| 5,550,050 A | 8/1996 | Holland et al. .......... 435/240.2 |
| 5,550,178 A | 8/1996 | Desai et al. .................. 524/56 |
| 5,552,267 A | 9/1996 | Stern et al. .................. 435/1.1 |
| 5,565,317 A | 10/1996 | Dohi et al. .................. 435/1.2 |
| 5,567,435 A | 10/1996 | Hubbell et al. ............. 424/426 |
| 5,569,462 A | 10/1996 | Martinson et al. .......... 424/424 |
| 5,569,463 A | 10/1996 | Helmus et al. .............. 424/426 |
| 5,573,934 A | 11/1996 | Hubbell et al. ............. 435/177 |
| 5,578,314 A | 11/1996 | Cochrum et al. ............ 424/424 |
| 5,578,442 A | 11/1996 | Desai et al. .................. 435/1.1 |
| 5,580,714 A | 12/1996 | Polovina ......................... 435/2 |
| 5,584,804 A | 12/1996 | Klatz et al. .................. 604/24 |
| 5,585,183 A | 12/1996 | Chu ......................... 428/402.2 |
| 5,587,309 A | 12/1996 | Rubin et al. ............. 435/240.2 |
| 5,593,440 A | 1/1997 | Brauker et al. ............... 623/11 |
| 5,593,673 A | 1/1997 | Dinsmore ................... 424/93.7 |
| 5,612,188 A | 3/1997 | Shuler et al. ................. 435/29 |
| 5,614,205 A | 3/1997 | Usala ........................ 424/424 |
| 5,620,883 A | 4/1997 | Shao et al. ................. 435/174 |
| 5,624,895 A | 4/1997 | Sobel ............................ 514/8 |
| 5,626,863 A | 5/1997 | Hubbell et al. .............. 424/426 |
| 5,629,194 A | 5/1997 | Dinsmore ................... 435/325 |
| 5,631,234 A | 5/1997 | Ozawa et al. ................. 514/19 |
| 5,635,344 A | 6/1997 | Garcia et al. ................ 435/1.1 |
| 5,635,609 A | 6/1997 | Levy et al. .................... 536/2 |
| 5,639,275 A | 6/1997 | Baetge et al. ............. 604/891.1 |
| 5,639,467 A | 6/1997 | Dorian et al. ............... 424/422 |
| 5,643,569 A | 7/1997 | Jain et al. ................... 424/93.7 |
| 5,643,594 A | 7/1997 | Dorian et al. ............... 424/424 |
| 5,643,773 A | 7/1997 | Aebischer et al. .......... 435/182 |
| 5,648,099 A | 7/1997 | Batich et al. ................ 424/497 |
| 5,651,976 A | 7/1997 | Price et al. .................. 424/409 |
| 5,651,980 A | 7/1997 | Lanza et al. ................ 424/424 |
| 5,653,687 A | 8/1997 | Mills et al. ................... 604/57 |
| 5,653,688 A | 8/1997 | Mills et al. ................... 604/57 |
| 5,653,756 A | 8/1997 | Clarke et al. ................. 623/11 |
| 5,656,468 A | 8/1997 | Dorian et al. ............... 435/178 |
| 5,656,469 A | 8/1997 | Tresco et al. ................ 435/182 |
| 5,656,481 A | 8/1997 | Baetge et al. ............... 435/325 |
| 5,659,055 A | 8/1997 | Franson et al. ............... 554/88 |
| 5,662,710 A | 9/1997 | Bonutti ........................ 623/11 |
| 5,672,361 A | 9/1997 | Halberstadt et al. ......... 424/556 |
| 5,674,289 A | 10/1997 | Fournier et al. ............... 623/11 |
| 5,677,174 A | 10/1997 | Dinsmore ................... 435/325 |
| 5,679,340 A | 10/1997 | Chappel .................... 424/93.1 |
| 5,679,565 A | 10/1997 | Mullen et al. ........... 435/240.1 |
| 5,681,587 A | 10/1997 | Halberstadt et al. ......... 424/562 |
| 5,686,113 A | 11/1997 | Speaker et al. ............. 424/490 |
| 5,686,418 A | 11/1997 | Culler ......................... 514/17 |
| 5,693,462 A | 12/1997 | Raymond ...................... 435/1 |
| 5,693,513 A | 12/1997 | Pope ......................... 435/176 |
| 5,693,514 A | 12/1997 | Dorian et al. ............... 435/178 |
| 5,696,152 A | 12/1997 | Southard .................... 514/449 |
| 5,696,175 A | 12/1997 | Mikos et al. ................. 521/61 |
| 5,699,793 A | 12/1997 | Brasile ....................... 128/630 |
| 5,700,848 A | 12/1997 | Soon-Shiong et al. ......... 522/7 |
| 5,702,444 A | 12/1997 | Struthers et al. .............. 623/11 |
| 5,705,270 A | 1/1998 | Soon-Shiong et al. ... 428/402.2 |
| 5,709,654 A | 1/1998 | Klatz et al. .................. 604/24 |
| 5,709,854 A | 1/1998 | Griffith-Cima et al. ..... 424/93.7 |
| 5,712,159 A | 1/1998 | Laurance et al. ......... 435/372.2 |
| 5,713,888 A | 2/1998 | Neuenfeldt et al. ....... 604/891.1 |
| 5,723,333 A | 3/1998 | Levine et al. ............... 435/325 |
| 5,725,854 A | 3/1998 | Selawry ..................... 424/93.7 |
| 5,733,336 A | 3/1998 | Neuenfeldt et al. ........... 623/11 |

| | | | |
|---|---|---|---|
| 5,736,397 A | 4/1998 | Garcia et al. | 435/374 |
| 5,738,673 A | 4/1998 | Mills et al. | 604/891.1 |
| 5,738,876 A | 4/1998 | Enevold | 424/486 |
| 5,739,020 A | 4/1998 | Pope | 435/176 |
| 5,739,033 A | 4/1998 | Soon-Shiong | 435/325 |
| 5,741,330 A | 4/1998 | Brauker et al. | 623/11 |
| 5,741,334 A | 4/1998 | Mullon et al. | 623/12 |
| 5,741,685 A | 4/1998 | Vacanti | 435/182 |
| 5,744,515 A | 4/1998 | Clapper | 523/113 |
| 5,747,325 A | 5/1998 | Newgard | 435/240.2 |
| 5,747,341 A | 5/1998 | Brothers | 435/404 |
| 5,750,507 A | 5/1998 | Ozawa et al. | 514/19 |
| 5,752,929 A | 5/1998 | Klatz et al. | 604/51 |
| 5,753,267 A | 5/1998 | Badylak et al. | 424/551 |
| 5,753,491 A | 5/1998 | Major et al. | 435/240.2 |
| 5,759,534 A | 6/1998 | Selawry | 424/93.7 |
| 5,759,578 A | 6/1998 | Soon-Shiong et al. | 424/484 |
| 5,759,830 A | 6/1998 | Vacanti et al. | 435/180 |
| 5,760,008 A | 6/1998 | Rubin | 514/25 |
| 5,762,922 A | 6/1998 | Noble et al. | 424/85.4 |
| 5,762,959 A | 6/1998 | Soon-Shiong et al. | 424/451 |
| 5,766,637 A | 6/1998 | Shine et al. | 424/497 |
| 5,766,873 A | 6/1998 | Noble et al. | 435/25 |
| 5,766,907 A | 6/1998 | Chang et al. | 435/178 |
| 5,770,417 A | 6/1998 | Vacanti et al. | 435/180 |
| 5,773,286 A | 6/1998 | Dionne et al. | 435/297.1 |
| 5,780,299 A | 7/1998 | Coon et al. | 435/366 |
| 5,782,912 A | 7/1998 | Brauker et al. | 623/11 |
| 5,783,216 A | 7/1998 | Faustman | 424/578 |
| 5,788,961 A | 8/1998 | Marklund et al. | 424/94.4 |
| 5,788,988 A | 8/1998 | Soon-Shiong et al. | 424/484 |
| 5,795,570 A | 8/1998 | Weber et al. | 424/93.7 |
| 5,795,726 A | 8/1998 | Glucksmann | 435/7.21 |
| 5,795,790 A | 8/1998 | Schinstine et al. | 435/382 |
| 5,798,113 A | 8/1998 | Dionne et al. | 424/422 |
| 5,800,529 A | 9/1998 | Brauker et al. | 623/11 |
| 5,800,828 A | 9/1998 | Dionne et al. | 424/422 |
| 5,800,829 A | 9/1998 | Dionne et al. | 424/422 |
| 5,801,033 A | 9/1998 | Hubbell et al. | 435/182 |
| 5,804,178 A | 9/1998 | Vacanti et al. | 424/93.7 |
| 5,807,406 A | 9/1998 | Brauker et al. | 623/11 |
| 5,820,882 A | 10/1998 | Hubbell et al. | 424/491 |
| 5,821,121 A | 10/1998 | Brothers | 435/325 |
| 5,824,331 A | 10/1998 | Usala | 424/424 |
| 5,846,530 A | 12/1998 | Soon-Shiong et al. | 424/93.7 |
| 5,863,715 A | 1/1999 | Rajotte et al. | 435/13 |
| 5,868,121 A | 2/1999 | Brown et al. | 123/526 |
| 5,955,457 A | 9/1999 | Lee et al. | 514/183 |
| 6,083,523 A | 7/2000 | Dionne et al. | 424/424 |

OTHER PUBLICATIONS

Charles et al.; *Viability of Cultured Microencapsulated Islets for Transplantation*, J. of Investigative Medicine, Biomedicine '98, Washington, DC May 1–3, 1998, p. 209.

Chicheportiche et al.; *In vitro kinetics of insulin release by microencapsulated rat islets: effect of the size of the microcapsules*, Diabetologia (1988) 31:54–57.

Fritschy et al.; *Effect of Alginate–Polylysine–Alginate Microencapsulation on In Vitro Insulin Release From Rat Pancreatic Islets*, Diabetes, vol. 40, Jan. 1991, pp. 37–43.

Garfinkel et al.; *Glutathione Potentiates Glucose–Stimulated Insulin Secretion in Isolated Porcine Islets*, Faseb J., H:A436, (Abstract #2520) 1997.

Garfinkel, et al.; *Optimization of the Microencapsulated Islet for Transplantation*, J. of Surgical Research, 76: 7–10 (1998).

Lacy et al.; *Prolongation of Islet Allograft Survival Following in vitro Culture (24°C) and a Single Injection of ALS*, Science, vol. 204, pp. 312–313, Apr. 1979.

Lafferty et al.; *Thyroid Allograft Immunogenicity Is Reduced after a Period in Organ Culture*, Science, 188:4183 pp. 259–261, Apr. 1975.

Littman et al.; *Glutathione–Mediated Preservation and Enhancement of Isolated Perifused Islet Function*, J. of Surgical Research 59:694–698 (1995).

Charles et al.; *Cryopreservation and microencapsulation of Islets*, American Pancreatic Association 1998 Meeting, 17:4 p. 429, Nov. 1998.

Ching et al., *Microencapsulation of Cryopreserved Islets forTransportation*, FASEB Journal, vol. 13, No. 4, pp. A216 (1999).

Hamaguchi et al., *Microencapsulation of pancreatic islets—A technique and its application to culture and transplantation*, Diabetes Research and Clinical Practice, vol. 2, No. 6, pp. 337–345 (1986).

Hua et al., *Morphological and Functional Studies on Microencapsulated Human Fetal Pancreatic Tissue*, Chinese Medical Journal, vol. 102, No. 10, pp. 786–790 (1989).

Janjic, et al., *Improved Insulin Secretion of Cryopreserved Human Islets by Antioxidant Treatment*, Pancrease, vol. 13, No. 2, pp. 166–172 (1996).

Leu, et al., *Microencapsultated Pancreatic Islets: A Pathological Study*, J. Formosan Med. Assoc., vol. 91, No. 9, pp. 849–858 (1992).

International Search Report; International Application No.PCT/US00/07515 dated Sep. 1, 2000.

MICROENCAPSULATED PANCREATIC ISLET CELLS

RELATED APPLICATIONS

This application is a divisional of U.S. Application Ser. No. 09/453,348 filed Dec. 1, 1999, now U.S. Pat. No. 6,365,385, which is a continuation-in-part of commonly owned, application Ser. No. 09/237,407, filed Mar. 22, 1999, now U.S. Pat No. 6,303,355, the disclosures of which are incorporated by reference herein in their entirety.

FIELD OF THE INVENTION

The present invention relates to methods of treating isolated pancreatic cells and microencapsulated pancreatic cells, in order to prepare the cells for transplantation. Media containing an antibiotic, an anti-oxidant, an anti-cytokine, or an anti-endotoxin, or combinations thereof, are utilized.

BACKGROUND OF THE INVENTION

Glycemic control in diabetes has been shown to delay the onset of, and slow the progression of, associated pathological complications. However, achieving adequate glycemic control using insulin therapy can be difficult. One alternative to insulin therapy is the transplantation of functioning pancreatic islet cells to diabetic subjects, to provide biological insulin replacement.

Approximately one percent of the volume of the human pancreas is made up of islets of Langerhans (hereinafter "islets"), which are scattered throughout the exocrine pancreas. Each islet comprises insulin producing beta cells as well as glucagon containing alpha cells, somatostatin secreting delta cells, and pancreatic polypeptide containing cells (PP-cells). The majority of islet cells are insulin-producing beta cells.

However, transplanted or grafted islet cells encounter immunological rejection, which can limit the clinical usefulness of his method. (Brunicardi and Mullen, *Pancreas* 9:281 (1994); Bartlett et al., *Transplant. Proc.* 26:737 (1994)). To combat rejection, immunosuppressive drugs may be used, but such immunosuppressive therapy impairs the body's immunological defenses and carries significant side effects and risks in itself. Approaches to containing and protecting transplanted islet cells have been proposed, including the use of extravascular diffusion chambers, intravascular diffusion chambers, intravascular ultrafiltration chambers, macroencapsulation and microencapsulation. The goal of islet transplantation is to achieve normoglycemia in the treated subject for some extended period of time.

Microencapsulation of islet cells has been proposed to reduce or avoid immunological rejection of transplanted islet cells. Lim and Sun, *Science* 210:908 (1980). The cells are encapsulated in a membrane that is permeable to cell substrates and cell secretions, but essentially impermeable to bacteria, lymphocytes, and large immunological proteins. The method of microencapsulation described by Lim and Sun involves forming gelled alginate droplets around isolated islet cells, and then adding coats of poly-L-lysine and additional alginate. The inner gelled core of the microcapsule is then liquefied by chelation. However, chelation of the core affects the structural support of the capsules and may adversely affect durability. The success of microencapsulated islet cell transplantation in treating diabetes depends on the ability of the microcapsules to provide sufficient amounts of insulin in response to glucose stimulation, over an extended period of time, to achieve adequate glycemic control.

Methods of treating isolated pancreatic cells, or of treating microencapsulated pancreatic cells, to enhance glucose-stimulated insulin production by the microcapsules and to provide durable microcapsules capable of glucose-stimulated insulin production, are therefore desirable.

SUMMARY OF THE INVENTION

A first aspect of the present invention is a method of treating isolated living cells, by first culturing the cells in a medium containing at least one of (or a combination of ): an antioxidant, an anti-cytokine, an anti-endotoxin, or an antibiotic. The cells are then microencapsulated in a biocompatible microcapsule that contains a hydrogel core and a semipermeable outer membrane, to provide a microcapsule containing living cells therein.

A further aspect of the present invention is a method of treating isolated living cells, by first cryopreserving the cells in a cryopreservation medium containing at least one of (or a combination of): an antioxidant, an anti-cytokine, an anti-endotoxin, or an antibiotic; then thawing the cells and encapsulating the cells in a biocompatible microcapsule having a hydrogel core and a semipermeable outer membrane.

A further aspect of the present invention is a method of treating biocompatible microcapsules containing living cells, where the microcapsule contains a hydrogel core and a semipermeable outer membrane. The microcapsules are cultured in a medium containing at least one of (or a combination of): an antioxidant, an anti-cytokine, an anti-endotoxin, or an antibiotic.

A further aspect of the present invention is a method of preparing microencapsulated cells by first culturing the cells in a cell culture medium containing at least one of (or a combination of): antioxidants, anti-cytokines, anti-endotoxins, and antibiotics. The cells are then encapsulated in a biocompatible microcapsule having a hydrogel core and a semipermeable outer membrane, where the living cells are present in the core. The microcapsules are then cultured in a medium containing at least one of (or a combination of): an antioxidant, an anti-cytokine, an anti-endotoxin, and an antibiotic.

A further aspect of the present invention is a method of preparing microencapsulated cells that includes a step of incubating the microencapsulated cells with a physiologically acceptable salt such as sodium sulfate or the like in order to produce a more durable, and therefore useful, biocompatible microcapsule.

A further aspect of the present invention is a method of isolating pancreatic islet cells in which an antioxidant is included in the digestion medium that is used to free the islet cells from pancreatic tissue.

A further aspect of the present invention is microencapsulated cell products, which may be produced by a process as described above.

DETAILED DESCRIPTION OF PREFERRED EMBODIMENTS

Figure 1:
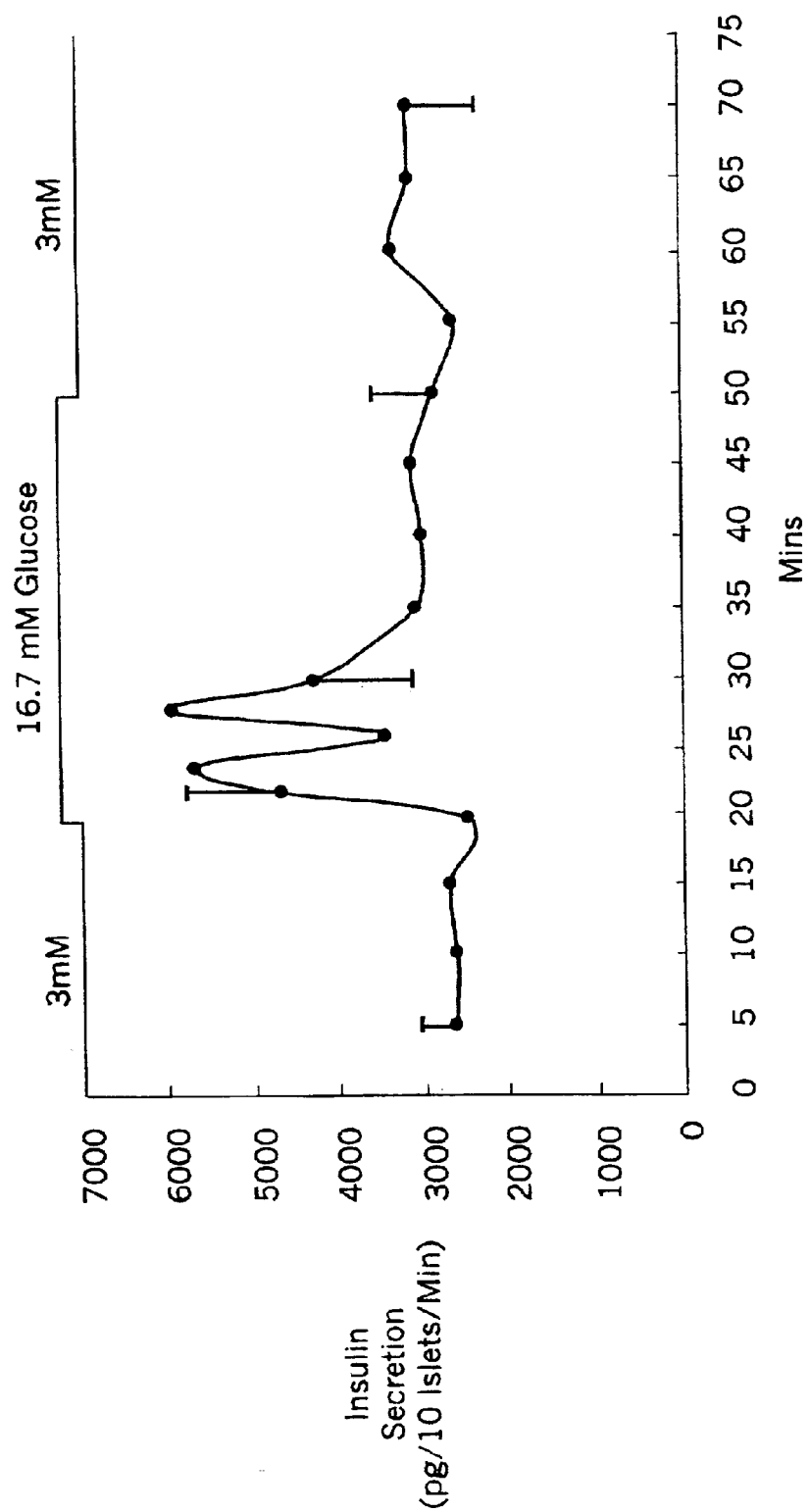
FIG. 1 graphs glucose-stimulated insulin secretion in control islets (n=4). Following a one hour period of preperifusion of unencapsulated islets with Krebs-Ringer Ringer-bicarbonate (KRB) containing 3.3 mM (basal) glucose, basal effluent perifusate was collected over 20 minutes. The glucose concentration in the perifusate was then raised to 16.7 mM and after 30 minutes of perifusion with sample collection, the glucose concentration was reduced to basal during another 20 minutes of perifusion.

The present inventors have determined that biocompatible microcapsules that contain living cells, such as pancreatic islet cells, benefit from a period of culture prior to use. Such culture enhances the ability of microcapsules containing islet cells to produce insulin in response to glucose stimulation. Culture of cell-containing microcapsules in a medium containing any of, or a combination of, an antibiotic, an anti-oxidant, an anti-cytokine, and an anti-endotoxin, is preferred.

The present inventors have further determined that cryopreservation of isolated cells (such as pancreatic islet cells) prior to microencapsulation does not adversely affect the function of the cells when subsequently encapsulated. Cryopreservation in a medium containing any of (or a combination of) an antibiotic, an anti-oxidant, an anti-cytokine, and an anti-endotoxin is preferred.

The present inventors have further determined that pre-culturing isolated cells prior to microencapsulation is beneficial. Culture of isolated islet cells prior to microencapsulation improves the glucose-stimulated insulin response of the encapsulated islets. Culture in a medium containing any of (or a combination of) an antibiotic, an anti-oxidant, an anti-cytokine, and an anti-endotoxin is preferred.

The above methods of treating cells and microcapsules may be combined, for example, by culturing isolated cells prior to microencapsulation and then culturing the resulting microcapsules.

Isolating Islets

Methods of isolating pancreatic islet cells are known in the art. Field et al., *Transplantation* 61:1554 (1996); Linetsky et al., *Diabetes* 46:1120 (1997). Fresh pancreatic tissue can be divided by mincing, teasing, comminution and/or collagenase digestion. The islets are then isolated from contaminating cells and materials by washing, filtering, centrifuging or picking procedures. Methods and apparatus for isolating and purifying islet cells are described in U.S. Pat. Nos. 5,447,863, 5,322,790, 5,273,904, and 4,868,121.

The isolated pancreatic cells may optionally be cultured prior to microencapsulation, using any suitable method of culturing islet cells as is known in the art. See e.g., U.S. Pat. No. 5,821,121. Isolated cells may be cultured in a medium under conditions that helps to eliminate antigenic components (*Transplant. Proc.*14:714–23 (1982)).

In general, a method of isolating pancreatic islet cells comprises (a) digesting pancreatic tissue with a digestion medium, the digestion medium containing an antioxidant, with the digesting step carried out for a time sufficient to produce free pancreatic islet cells suitable for subsequent harvesting; and then (b) collecting the free pancreatic islet cells to produce isolated pancreatic islet cells. The antioxidant is included in the digestion medium in an amount sufficient to inhibit reoxygenation injury of the isolated pancreatic islet cells (e.g., from about 0.05, 0.1, or 0.5 milliMolar to about 5, 10 or 20 milliMolar or more) The antioxidant is preferably one that is not itself digested in the digestion medium, such as a vitamin or organic chemical antioxidants. Examples of suitable antioxidants include, but are not limited to, vitamin C, vitamin E, vitamin K, lipoic acid, lazaroids, and butylated hydroxyanisole. Once collected, the isolated pancreatic islet cells may be cultured and microencapsulated as further described herein.

A preferred method for isolating viable islet cells, such as porcine islet cells, is as follows. Adult pigs (approximately 25–20 kg) are anesthetized, followed by intra-arterial infusion of ice-cold UW solution and complete pancreatectomy. The pancreatic duct is cannulated for infusion of digestion medium comprising an antioxidant. An exemplary digestion medium is Hanks' balanced salt solution containing collagenase type P (1.5 mg/ml), DNase 1 (10,000 units) and TROLOX® brand water soluble vitamin E antioxidant (1 mM). After 20 minutes incubation on ice, the pancreas is incubated at 37° C. for 20 minutes before being hand-shaken for one minute. Digested tissue is filtered, and islet clusters are separated using OPTIPREP® gradient, washed in Hanks' solution and identified by dithizone staining. This method utilizes an anti-oxidant in the digestion medium and hand-shaking, and does not require special isolation chambers or mechanical disruption of the pancreatic tissue.

Microencaosulation Techniques

Microencapsulation of islet cells generally involves three steps: (a) generating microcapsules enclosing the islet cells (e.g., by forming droplets of cell-containing liquid alginate followed by exposure to a solution of calcium chloride to form a solid gel), (b) coating the resulting gelled spheres with additional outer coatings (e.g., outer coatings comprising polylysine and/or polyornithine) to form a semipermeable membrane; and (c) liquefying the original core gel (e.g., by chelation using a solution of sodium citrate). The three steps are typically separated by washings in normal saline.

A preferred method of microencapsulating pancreatic cells is the alginate-polyamino acid technique. Briefly, islet cells are suspended in sodium alginate in saline, and droplets containing islets are produced. Droplets of cell-containing alginate flow into calcium chloride in saline. The negatively charged alginate droplets bind calcium and form a calcium alginate gel. The microcapsules are washed in saline and incubated with poly-L-lysine or poly-L-ornithine (or combinations thereof); the positively charged poly-l-lysine and/or poly-L-ornithine displaces calcium ions and binds (ionic) negatively charged alginate, producing an outer polyelectrolyte membrane. A final coating of sodium alginate may be added by washing the microcapsules with a solution of sodium alginate, which ionically bonds to the poly-L-lysine and/or poly-L-ornithine layer. See U.S. Pat. No.

4,391,909 to Lim et al (all US patents referenced herein are intended to be incorporated herein in their entirety). This technique produces what has been termed a "single-wall" microcapsule. Preferred microcapsules are essentially round, small, and uniform in size. Wolters et al., *J. Appli Biomater.* 3:281 (1992).

When desired, the alginate-polylysine microcapsules can then be incubated in sodium citrate to solubilize any calcium alginate that has not reacted with poly-1-lysine, i.e., to solubilize the internal core of sodium alginate containing the islet cells, thus producing a microcapsule with a liquefied cell-containing core portion. See Lim and Sun, *Science* 210:908 (1980). Such microcapsules are referred to herein as having "chelated", "hollow" or "liquid" cores.

A "double-wall" microcapsule is produced by following the same procedure as for single-wall microcapsules, but prior to any incubation with sodium citrate, the microcapsules are again incubated with poly-1-lysine and sodium alginate.

Alginates are linear polymers of mannuronic and guluronic acid residues. Monovalent cation alginate salts, e.g., Na-alginate, are generally soluble. Divalent cations such as Ca++, Ba++ or Sr++ tend to interact with guluronate, providing crosslinking and forming stable alginate gels. Alginate encapsulation techniques typically take advantage of the gelling of alginate in the presence of divalent cation solutions. Alginate encapsulation of cells generally involves suspending the cells to be encapsulated in a solution of a monovalent cation alginate salt, generating droplets of this solution, and contacting the droplets with a solution of divalent cations. The divalent cations interact with the alginate at the phase transition between the droplet and the divalent cation solution, resulting in the formation of a stable alginate gel matrix being formed. A variation of this technique is reported in U.S. Pat. No. 5,738,876, wherein the cell is suffused with a solution of multivalent ions (e.g., divalent cations) and then suspended in a solution of gelling polymer (e.g., alginate), to provide a coating of the polymer.

Chelation of the alginate (degelling) core solubilizes the internal structural support of the capsule, may adversely affect the durability of the microcapsule, and is a harsh treatment of the encapsulated living cells. Degelling of the core may also cause leaching out of the unbound poly-lysine or solubilized alginate, resulting in a fibrotic reaction to the implanted microcapsule. The effect of core liquidation on glucose-stimulated insulin secretion by the encapsulated cells has been studied. Fritschy et al., *Diabetes* 40:37 (1991). The present inventors examined the function of islets enclosed in microcapsules that had not been subjected to liquefaction of the core (i.e., 'solid' or non-chelated microcapsules). It was found that culture of solid microcapsules prior to use enhanced the insulin response of the enclosed islets to glucose stimulation.

Alginate/polycation encapsulation procedures are simple and rapid, and represent a promising method for islet encapsulation for clinical treatment of diabetes. Many variations of this basic encapsulation method have been described in patents and the scientific literature. Chang et al., U.S. Pat. No. 5,084,350 discloses microcapsules enclosed in a larger matrix, where the microcapsules are liquefied once the microcapsules are within the larger matrix. Tsang et al., U.S. Pat. No. 4,663,286 discloses encapsulation using an alginate polymer, where the gel layer is cross-linked with a polycationic polymer such as polylysine, and a second layer formed using a second polycationic polymer (such as polyornithine); the second layer can then be coated by alginate. U.S. Pat. No. 5,762,959 to Soon-Shiong et al. discloses a microcapsule having a solid (non-chelated) alginate gel core of a defined ratio of calcium/barium alginates, with polymer material in the core.

U.S. Pat. Nos. 5,801,033 and 5,573,934 to Hubbell et al. describe alginate/polylysine microspheres having a final polymeric coating (e.g., polyethylene glycol (PEG)); Sawhney et al., Biomaterials 13:863 (1991) describe alginatepolylysine microcapsules incorporating a graft copolymer of poly-1-lysine and polyethylene oxide on the microcapsule surface, to improve biocompatibility; U.S. Pat. No. 5,380,536 describes microcapsules with an outermost layer of water soluble non-ionic polymers such as polyethylene(oxide). U.S. Pat. No. 5,227,298 to Weber et al. describes a method for providing a second alginate gel coating to cells already coated with polylysine alginate; both alginate coatings are stabilized with polylysine. U.S. Pat. No. 5,578,314 to Weber et al. provides a method for microencapsulation using multiple coatings of purified alginate.

U.S. Pat. No. 5,693,514 to Dorian et al. reports the use of a non-fibrogenic alginate, where the outer surface of the alginate coating is reacted with alkaline earth metal cations comprising calcium ions and/or magnesium ions, to form an alkaline earth metal alginate coating. The outer surface of the alginate coating is not reacted with polylysine.

U.S. Pat. No. 5,846,530 to Soon-Shiong describes microcapsules containing cells that have been individually coated with polymerizable alginate, or polymerizable polycations such as polylysine, prior to encapsulation.

Microcapsules

The methods of the present invention are intended for use with any microcapsule that contains living cells secreting a desirable biological substance (preferably pancreatic cells and more preferably islet cells), where the microcapsule comprises an inner gel or liquid core containing the cells of interest, or a liquid core containing the cells of interest, bounded by a semi-permeable membrane surrounding the cell-containing core. The inner core is preferably composed of a water-soluble gelling agent; preferably the water-soluble gelling agent comprises plural groups that can be ionized to form anionic or cationic groups. The presence of such groups in the gel allows the surface of the gel bead to be cross-linked to produce a membrane, when exposed to polymers containing multiple functionalities having a charge opposite to that of the gel.

Cells suspended in a gellable medium (such as alginate) may be formed into droplets using any suitable method as is known in the art, including but not limited to emulsification (see e.g., U.S. Pat. No. 4,352,883), extrusion from a needle (see, e.g., U.S. Pat. No. 4,407,957; Nigam et al., *Biotechnology Techniques* 2:271–276 (1988)), use of a spray nozzle (Plunkett et al., *Laboratory Investigation* 62:510–517 (1990)), or use of a needle and pulsed electrical electrostatic voltage (see, e.g., U.S. Pat. Nos. 4,789,550; 5,656,468).

The water-soluble gelling agent is preferably a polysaccharide gum, and more preferably a polyanionic polymer. An exemplary water-soluble gelling agent is an alkali metal alginate such as sodium alginate. The gelling agent preferably has free acid functional groups and the semi-permeable membrane is formed by contacting the gel with a polymer having free amino functional groups with cationic charge, to form permanent crosslinks between the free amino acids of the polymer and the acid functional groups. Preferred polymers include polylysine, polyethylenimine, and polyarginine. A particularly preferred microcapsule contains cells immobilized in a core of alginate with a poly-lysine coating; such microcapsules may comprise an additional external alginate layer to form a multi-layer alginate-polylysine-alginate microcapsule. See U.S. Pat. No. 4,391,909 to Lim et al, the contents of which are incorporated by reference herein in their entirety.

When desired, the microcapsules may be treated or incubated with a physiologically acceptable salt such as sodium sulfate or like agents, in order to increase the durability of the microcapsule, while retaining or not unduly damaging the physiological responsiveness of the cells contained in the microcapsules. By "physiologically acceptable salt" is meant a salt that is not unduly deleterious to the physiological responsiveness of the cells encapsulated in the microcapsules. In general, such salts are salts that have an anion that binds calcium ions sufficiently to stabilize the capsule, without substantially damaging the function and/or viability of the cells contained therein. Sulfate salts, such as sodium sulfate and potassium sulfate, are preferred, and sodium sulfate is most preferred. The incubation step is carried out in an aqueous solution containing the physiological salt in an amount effective to stabilize the capsules, without substantially damaging the function and/or viability of the cells contained therein as described above. In general, the salt is included in an amount of from about 0.1 or 1 milliMolar up to about 20 or 100 millimolar, most preferably about 2 to 10 millimolar. The duration of the incubation step is not critical, and may be from about 1 or 10 minutes to about 1 or 2 hours, or more (e.g., over night). The temperature at which the incubation step is carried out is likewise not critical, and is typically from about 4 degrees Celsius up to about 37 degrees Celsius, with room temperature (about 21 degrees Celsius) preferred.

When desired, liquefaction of the core gel may be carried out by any suitable method as is known in the art, such as ion exchange or chelation of calcium ion by sodium citrate or EDTA. Microcapsules useful in the present invention thus have at least one semipermeable surface membrane surrounding a cell-containing core. The surface membrane permits the diffusion of nutrients, biologically active molecules and other selected products through the surface membrane and into the microcapsule core. The surface membrane contains pores of a size that determines the molecular weight cut-off of the membrane. Where the microcapsule contains insulin-secreting cells, the membrane pore size is chosen to allow the passage of insulin from the core to the external environment, but to exclude the entry of host immune response factors.

As used herein, a "poly-amino acid-alginate microsphere" refers to a capsule of less than 2 mm in diameter having an inner core of cell-containing alginate bounded by a semipermeable membrane formed by alginate and poly-1-lysine. Viable cells encapsulated using an anionic polymer such as alginate to provide a gel layer, where the gel layer is subsequently cross-linked with a polycationic polymer (e.g., an amino acid polymer such as polylysine. See e.g., U.S. Pat. Nos. 4,806,355, 4,689,293 and 4,673,566 to Goosen et al.; U.S. Pat. Nos. 4,409,331, 4,407,957, 4,391,909 and 4,352,883 to Lim et al.; U.S. Pat. Nos. 4,749,620 and 4,744,933 to Rha et al.; and U.S. Pat. No. 5,427,935 to Wang et al. Amino acid polymers that may be used to encapsulate islet cells in alginate include the cationic amino acid polymers of lysine, arginine, and mixtures thereof.

Culture of Isolated Cells

Generally, pancreatic islets are isolated by collagenase digestion of pancreatic tissue. This process involves subjecting the islet cells to a period of hypoxia which is then followed by reoxygenation. Hypoxia-reoxygenation produces an injury that is linked to excessive production of oxygen free radicals which impair the function, and cause the death, of islet cells, particularly those isolated from the pancreas of large mammals such as pigs and humans.

The present inventors have determined that culture of isolated islets or islet cells prior to microencapsulation is beneficial. The islets are cultured according to known cell culture techniques for a period of at least 3 hours, more preferably from 12–36 hours, and more preferably from 18–24 hours, in a culture medium containing an antioxidant compound. More preferably, the culture medium contains any one of, or any combination of, the following: an antioxidant, an anti-cytokine, an anti-endotoxin, and an antibiotic.

Culture of isolated pancreas cells to improve glucose-stimulated insulin secretion may utilize any suitable antioxidant as is known in the art. As used herein, an antioxidant is a compound that neutralizes free radicals or prevents or suppresses the formation of free radicals. Particularly preferred are molecules including thiol groups such as reduced glutathione (GSH) or its precursors, glutathione or glutathione analogs, glutathione monoester, and N-acetylcysteine. Other suitable anti-oxidants include superoxide dismutase, catalase, vitamin E, Trolox, lipoic acid, lazaroids, butylated hydroxyanisole (BHA), vitamin K, and the like. Glutathione, for example, may be used in a concentration range of from about 2 to about 10 mM. See, e.g., U.S. Pat. Nos. 5,710,172; 5,696,109; 5,670,545.

Culture of isolated pancreas cells to improve glucose-stimulated insulin secretion may utilize any suitable antibiotic as is known in the art. Suitable antibiotics include penicillins, tetracyclines, cephalosporins, macrolides, β-lactams and aminoglycosides; examples of such suitable antibiotics include streptomycin and amphotericin B.

Culture of isolated pancreas cells to improve glucose-stimulated insulin secretion may utilize any suitable anti-cytokine as is known in the art. Cytokines are proteins secreted by many different cell types, that regulate the intensity and duration of immune responses. Cytokines include various growth factors, colony-stimulating factors, interleukins, lymphokines, monokines and interferons. Anti-cytokines are compounds that prevent or suppress the function of cytokines. Suitable anti-cytokines for use in culturing islet cells include dimethylthiourea (10 mM), citiolone (5 mM), pravastatin sodium (PRAVACHOL®, 20 mg/kg), L-N$^G$-monomethylarginine (L-NMMA, 2 mM), lactoferrin (100 µg/ml), 4-methylprednisolone (20 µg/ml), and the like.

Culture of isolated pancreas cells to improve glucose-stimulated insulin secretion may utilize any suitable anti-endotoxin as is known in the art. Endotoxins are bacterial toxins, complex phospholipid-polysaccharide molecules that form a part of the cell wall of a variety of Gram-negative bacteria. Anti-endotoxins are compounds that destroy or inhibit the activity of endotoxins. Endotoxins are intracellular toxins, and are complex phospholipid-polysaccharide macromolecules that form a part of the cell wall of a variety of Gram-negative bacteria, including enterobacteria, vibrios, brucellae and neisseriae. Suitable anti-endotoxins for use in culturing islet cells include L-N$^G$-Monomethylarginine (L-NMMA, 2 mM), lactoferrin (100 µg/ml), N-acetylcysteine (NAC, 1 mM), adenosine receptor antagonists such as bamiphylline (theophylline) and anti-lipopolysaccharide compounds such as echinomycine (10 nM), and the like.

Cryopreservation of Cells

Mammalian tissue remains viable in vitro only for short periods of time, usually days. Loss of islet cells suitable for transplantation may be avoided by viable cryopreservation and cold storage of the cells. The present inventors determined that microencapsulated islet cells respond poorly to cryopreservation. However, cryopreservation of naked (unencapsulated) islet cells did not adversely affect their later function in microcapsules when the cells were first cryopreserved, then thawed and microencapsulated. Frozen and thawed microencapsulated islets responded poorly to glucose stimulation; in comparison, 'naked' islet cells that were cryopreserved and then thawed retained their ability to respond to glucose stimulation and were suitable for microencapsulation. Islet cells can thus be preserved by cryopreservation, thawed and microencapsulated just prior to use.

Methods of cryopreservation are well known in the art. In general terms, cryopreservation of animal cells involves freezing the cells in a mixture of a growth medium and another liquid that prevents water from forming ice crystals, and then storing the cells at liquid nitrogen temperatures (e.g., from about −80 to about −196° C.).

An aspect of the present invention is the cryopreservation of isolated mammalian cells in a cryopreservation medium containing an antioxidant, followed by microencapsulation of the cells prior to in vivo implantation. A preferred embodiment of the present invention is the cryopreservation of isolated islets or islet cells in a cryopreservation medium containing an antioxidant as described herein, followed by microencapsulation prior to in vivo implantation.

More preferably, the cells are cryopreserved in a medium containing at least one of, or a combination of, the following: an antioxidant, an anti-cytokine, an anti-endotoxin, and an antibiotic (each as described above). Preferably, the cells are cryopreserved in a medium containing at least one each of an antioxidant, an anti-cytokine, an anti-endotoxin, and an antibiotic (each as described above).

Culture of Microspheres.

The present inventors studied the response to glucose of islet-containing microcapsules, and found that culture of such microcapsules prior to use enhanced subsequent glucose-stimulated insulin production. The enclosed islets responded better to a glucose challenge than islets contained in fresh (non-cultured) microcapsules.

Culture of microencapsulated cells is carried out in a manner similar to the culture of isolated cells, as described herein and as generally known in the art. Accordingly, a method of the present invention is the culture of microcapsules (with either solid or liquid cores containing living cells) prior to implantation in vivo, to enhance or improve the ability of the microcapsule to produce a desired cell secretory product. A particularly preferred embodiment is the culture, prior to implantation, of gelled or solid-core alginate-polylysine microcapsules containing pancreatic islets or islet cells. Microcapsules are cultured for a period of at least 3 hours, more preferably from 12 to 36 hours, or 18 to 24 hours, prior to implantation.

Preferably the microcapsules are cultured in a medium containing at least one of, or a combination of, the following: an antibiotic, an antioxidant, an anticytokine, and an antiendotoxin (as described above). More preferably, the microcapsules are cultured in a medium containing at least one each of an antioxidant, an anti-cytokine, an anti-endotoxin, and an antibiotic (each as described above).

As noted above, microencapsulated islet cells are also an aspect of this invention. In general, such microencapsulated islet cells comprise a microcapsule containing living pancreatic islet cells therein, the microencapsulated islet cells exhibiting a weight gain of not more than 1, 5 or 10 percent by weight over a period of one month in physiological saline solution at 37 degrees Celsius (exhibiting the durability thereof) and exhibiting at least 150, 200 or 250 percent basal insulin secretion in response to 16.7 millimolar glucose challenge in Krebs-Ringer physiological solution at pH 7.4 after said period of one month. Such microencapsulated cells may be produced by the procedures described herein, preferably including the step of incubating them with a physiologically acceptable salt to enhance the durability or stability of the capsule as described above.

Transplantation

Encapsulated islet cells produced according to the present invention may be transplanted into subjects as a treatment for insulin-dependent diabetes; such transplantation may be into the peritoneal cavity of the subject. An amount of encapsulated islet cells to produce sufficient insulin to control glycemia in the subject is provided by any suitable means, including but not limited to surgical implantation and intraperitoneal injection. The International Islet Transplant Registry has recommended transplants of at least 6,000 islets, equivalent to 150 $\mu$m in size, per kilogram of recipient body weight, to achieve euglycemia. However, it will be apparent to those skilled in the art that the quantity of microcapsules transplanted depends on the ability of the microcapsules to provide insulin in vivo, in response to glucose stimulation. One skilled in the art will be able to determine suitable transplantation quantities of microcapsules, using techniques as are known in the art.

Definitions

As used herein, materials that are intended to come into contact with biological fluids or tissues (such as by implantation or transplantation into a subject) are termed "biomaterials". It is desirable that biomaterials induce minimal reactions between the material and the physiological environment. Biomaterials are considered "biocompatible" if, after being placed in the physiological environment, there is minimal inflammatory reaction, no evidence of anaphylactic reaction, and minimal cellular growth on the biomaterial surface. Upon implantation in a host mammal, a biocompatible microcapsule does not elicit a host response sufficient to detrimentally affect the function of the microcapsule; such host responses include formation of fibrotic structures on or around the microcapsule, immunological rejection of the microcapsule, or release of toxic or pyrogenic compounds from the microcapsule into the surrounding host tissue.

The term "encapsulate" as used herein refers to the containment of a cell or cells within a capsule delineated by a physical barrier (i.e., a barrier that reduces or controls the permeability of the capsule). The term "microcapsule" or "microsphere" as used herein refers to a structure containing a core of biological substance (such as cells) in an aqueous medium, surrounded by a semi-permeable membrane, and having a diameter of no more than 2 mm. Preferably, microspheres are from about 3$\mu$m to about 2 mm in diameter. More preferably, microcapsules range from about 50$\mu$m to about 1,000 $\mu$m in diameter, or from about 300 $\mu$m to about 500 $\mu$m in diameter. Depending on the method of microencapsulation used, it will be apparent that the microcapsule wall or membrane may also contain some cells therein.

As used herein, culture refers to the maintenance or growth of cells on or in a suitable nutrient medium, after removal of the cells from the body. Suitable nutrient culture media are readily available commercially, and will be apparent to those skilled in art given the cell type to be cultured.

The term "cells" as used herein refers to cells in various forms, including but not limited to cells retained in tissue, cell clusters (such as pancreatic islets or portions thereof), and individually isolated cells.

EXAMPLE 1

Materials and Methods

Materials

Male Sprague-Dawley rats weighing 200–300 g were obtained (Charles River). Collagenase (Type P) was obtained from Boehringer Mannheim Co. (Indianapolis, Ind.). Highly purified bovine serum albumin (BSA, fraction V) free of fatty acids and insulin-like activity and all chemicals for buffer and encapsulation Solution were obtained from Sigma Chemical Co. (St. Louis, Mo.). Monoiodinated $^{125}$I-insulin was obtained from New England Nuclear (Boston, Mass.).

Islet Isolation

Islets were isolated by collagenase digestion: (Lacy et al., *Diabetes* 16:35 (1967)). Rats were anesthetized with intraperitoneal pentobarbital, laparotomy was performed, and the pancreatic duct was cannulated. The pancreas was distended by infusing 15 ml Hank's Balanced Salt Solution (HBSS). Pancreatectomy was performed, and the pancreas was digested in collagenase solution (1.5 mg/ml) at 37° C. for 25 minutes. The digested tissue was filtered through a mesh and then washed several times in chilled HBSS and placed under a dissecting microscope. At least 400 islets/experiment were purified by being handpicked and placed in chilled HBSS until microencapsulation.

Microencapsulation

Islets were suspended in 1.4% sodium alginate and placed in a droplet generator adapted from that of Walters et al., *J. Appl. Biomater.* 3:281 (1992). Droplets generated from islets suspended in the alginate solution were collected in a funnel containing 1.1% $CaCl_2$, where they gelled. The resulting microcapsules were washed with normal saline (NS), incubated with 0.05% poly-L-lysine, washed again with NS, incubated with alginate, and washed a final time with NS. These islet-containing microcapsules were then split into three groups. Group II islets were set aside for immediate perifusion. Group III islets were also set aside without chelation, for 24 hours of culture in RPMI 1640 at 37° C. prior to perifusion. In Group I islets, the alginate core of the microcapsule was liquefied by incubation with a chilled 55 mM sodium citrate solution for seven minutes, to chelate the central alginate-$Ca^{2+}$ core.

Perifusion

Unencapsulated and microencapsulated islets were perifused by a method previously described (Garfinkel et al., *J. Surg. Res.* 52:328 (1992)). In each case, 30 islets were handpicked under a stereomicroscope and placed (10/chamber) in a plastic flow-through perifusion chamber (Millipore Corp.). Islets were perifused for 1 hour at 37° C., at the rate of 1 ml/min, with a modified Krebs-Ringer-bicarbonate (KRB) solution (Opara et al., *Endocrinology* 130:657 (1992)), containing 1% BSA and a basal 3.3 mM (60 mg/dl) glucose, maintained at pH 7.4 by continuous gassing with 95% $O_2$/5%$CO_2$, in an unsealed reservoir. All perifusion experiments were conducted with triplicate chambers housing islets from the same preparation, with each chamber receiving microencapsulated islets prepared under one of the three conditions described above.

After the 1-hour perifusion, basal effluent samples were periodically collected on ice for 20 minutes before islets were then perifused with the KRB solution containing 16.7 mM glucose (300 mg/dl) for 30 minutes, during which samples were again collected at intervals. Following the 16.7 mM glucose stimulation, a washout perifusion with the 3.3 mM glucose buffer was performed for 20 minutes with sample collection. Solutions were changed using a stopcock and all effluent perifusate samples obtained throughout the study were stored frozen at −20° C. until radioimmunoassay for insulin (Herbert et al., *J. Clin. Endocrinol. Metab.* 25:1375 (1965)).

Data Analysis

Results are expressed as mean±SEM. Results were plotted as rates of insulin secretion (pg insulin/10 islets/minute) versus time. Peak rates of insulin secretion during the first stimulatory phase were compared with basal rates within the same group, using a Student's t test. For comparisons among groups, an analysis of variance (ANOVA) computer program was used and depending on the outcome of ANOVA, the Bonferroni correction was made. In all cases, significance was defined as $P<0.05$.

EXAMPLE 2

Response of Isolated and Encapsulated Islets to Glucose

Control Islets

Unencapsulated islets were first perifused with the high 16.7 mM glucose to determine the normal isolated islet response to stimulation with this concentration of glucose. The results are presented in FIG. 1 (representing four experiments) with a mean basal rate of insulin secretion of 2650±40 pg/10 islets/minute.

When the glucose concentration in the perifusate was raised to 16.7 mM, insulin response of the islets was biphasic, with a mean rate of 5120±310 pg/10 islets/minute ($P<0.002$ versus basal), which subsequently returned to basal upon switching back to basal perifusion (FIG. 1).

Experimental Islets Groups I, II, and III

Figure 2:
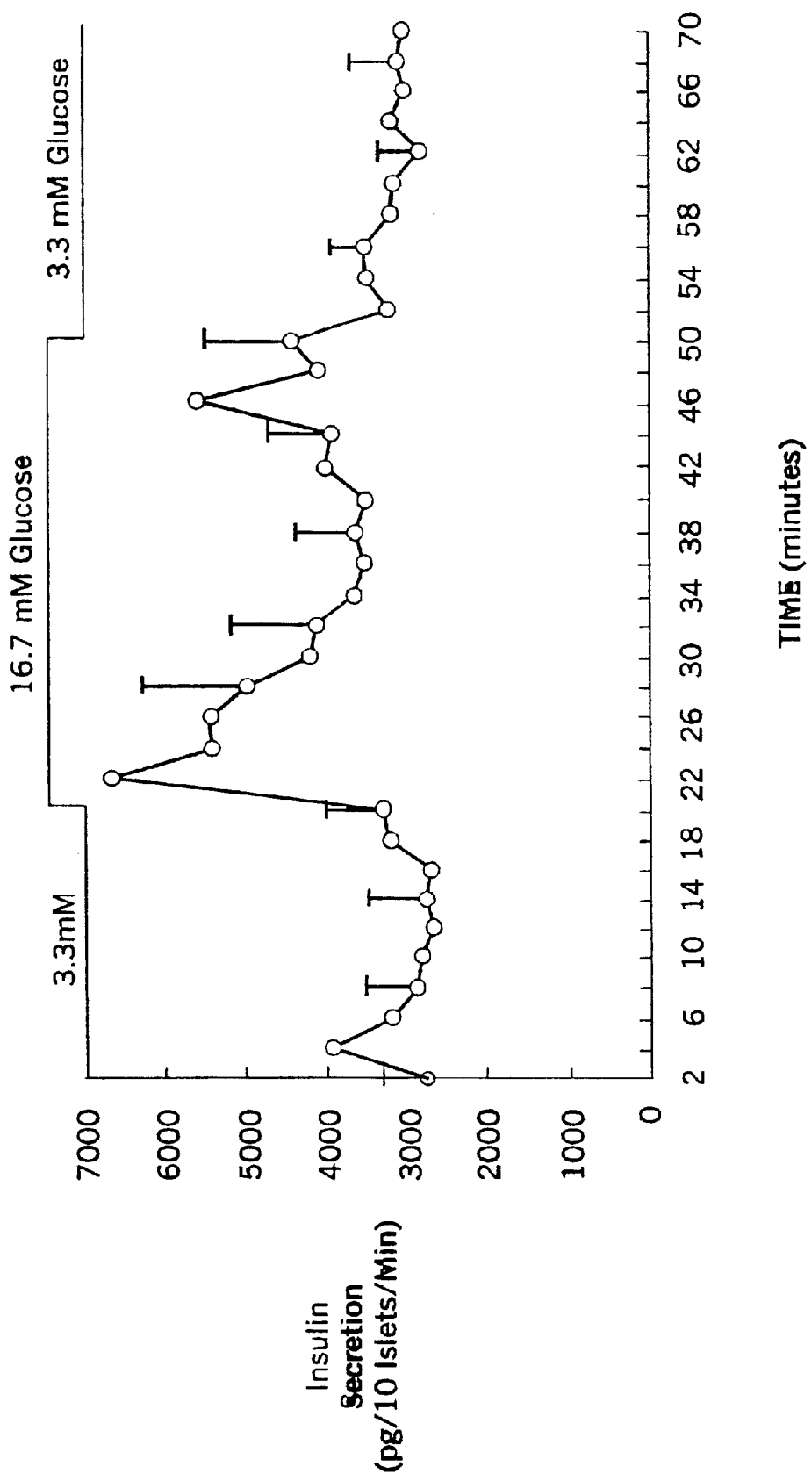
FIG. 2 graphs the effect of chelation on the microcapsular core. Using the protocol described for FIG. 1, above, islets enclosed in microcapsules with a liquefied (chelated) core were tested for glucose-stimulated insulin production.

Group I islets (liquefied core microcapsules) responded similarly as compared to control islets with a biphasic response to the stimulatory concentration of glucose (FIG. 2). In six experiments, insulin secretion increased from a basal rate of 3005±647 pg/10 islets/minute to a stimulated rate of 5164±1428 pg/10 islets/minute ($P<0.05$), during the first phase secretion in response to stimulation with 16.7 mM glucose. As noted in control unencapsulated islets (FIG. 1), in Group I islets, the rate of insulin secretion returned to basal after withdrawal of the stimulatory 16.7 mM glucose (FIG. 2).

Figure 3:
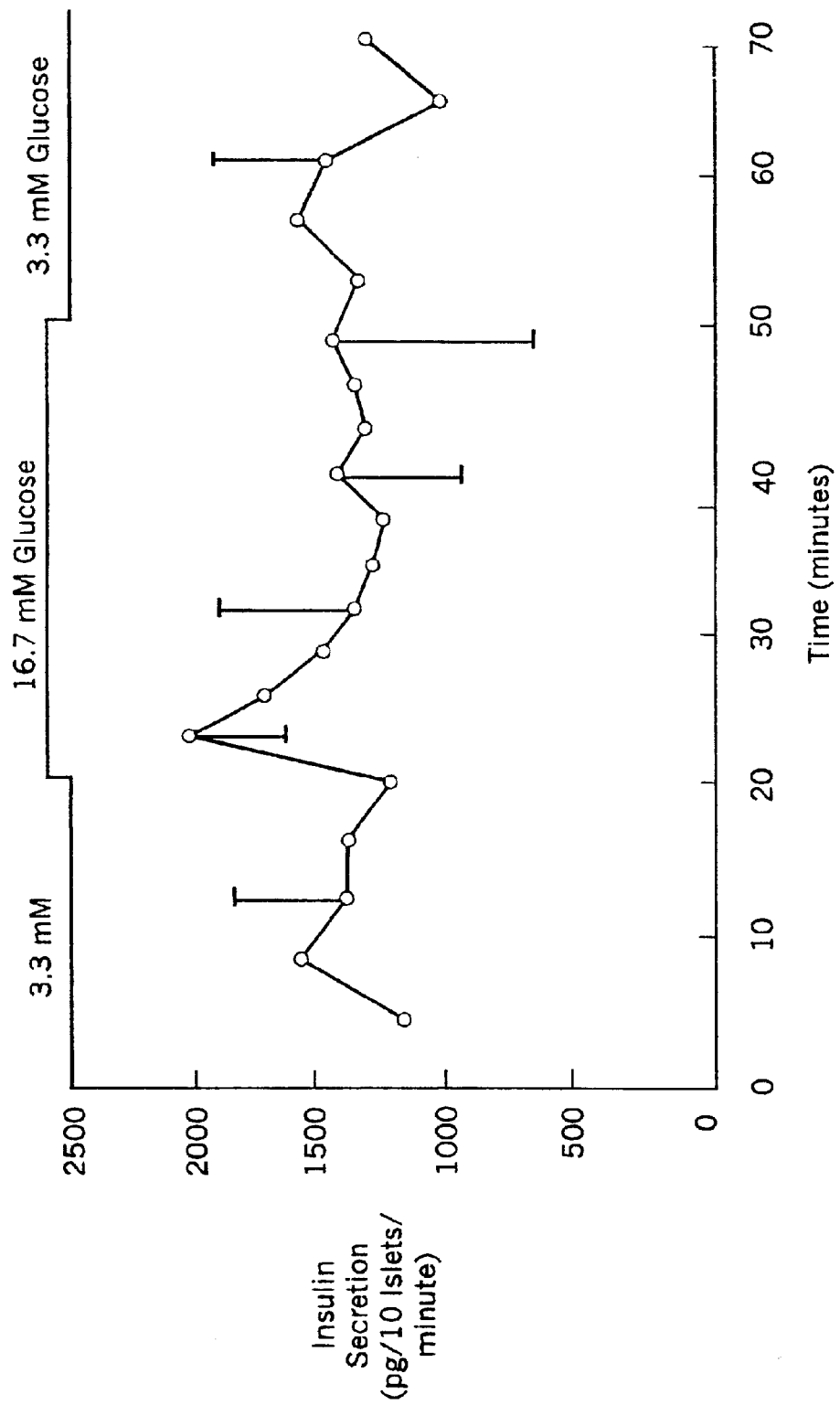
FIG. 3 graphs glucose stimulation of islets in unchelated microcapsules. Using the protocol described for FIG. 1, above, islets enclosed in microcapsules with a gelled (unchelated) core were tested for glucose-stimulated insulin production.

In contrast, Group II islets (gelled core microcapsules, n=6) had a lower basal rate of insulin secretion (1740±219 pg/10 islets/minutes, $P<0.05$ vs. Group I basal). These islets did not significantly respond to 16.7 mM glucose stimulation (FIG. 3).

Figure 4:
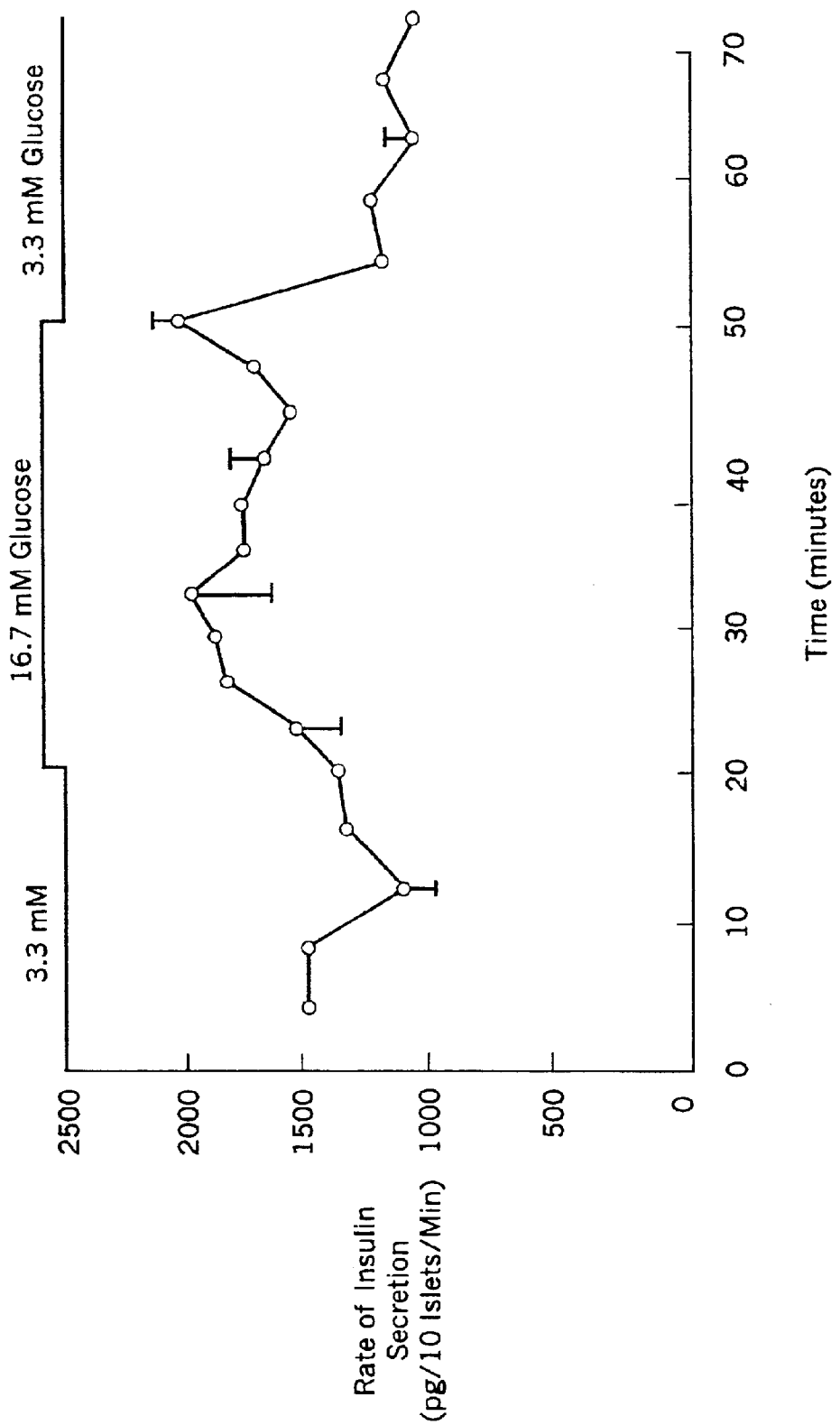
FIG. 4 graphs the effect of 24 hours of culture on gelled (unchelated) microcapsule function. Following microencapsulation of islets without chelation, the microcapsules were cultured in RPMI 1640 medium for 24 hours prior to testing the response of the enclosed islets to glucose stimulation.

Group III islets (FIG. 4), which represent cultured gelled core microcapsules, also had a lower basal rate of insulin secretion (1375±161 pg/10 islets/minutes) than control islets, as well as those in Groups I and II ($P<0.05$). However, in contrast to the freshly perifused gelled core microcapsules (Group II), the islets in the cultured gelled-core microcapsules (Group III) had a small but significant increase in their rate of insulin secretion in response to 16.7 mM glucose stimulation ($P<0.05$, n=6) as shown in FIG. 4, and in Table 1 which summarizes the data from the control and the three experimental groups.

TABLE 1

| Group | Basal (3.3 mM) | 16.7 mM |
|---|---|---|
| Control | 2650 ± 40 | 5120 ± 310* |
| Group I (liquefied core) | 3005 ± 647 | 5164 ± 1428** |
| Group II (gelled core, no culturing) | 1740 ± 219 | 1707 ± 181 |
| Group III (gelled core, cultured) | 1375 ± 131 | 1835 ± 182*** |

*$P < 0.002$ vs. basal, n = 4
**$P < 0.05$ vs. basal, n = 6
***$P < 0.05$ vs. basal, n = 6

EXAMPLE 3

Response to Glucose: Fresh and Frozen Microencapsulated Islets

The function of cryopreserved, microencapsulated islet cells, and the stability of the capsule, was studied.

Islets were isolated from Sprague-Dawley rats by collagenase digestion of pancreatic tissue, and microencapsulated in polylysine-alginate using a syringe-air-droplet generator. Aliquots of fresh unencapsulated (group 1) and encapsulated (group 2) islets were taken for determination of glucose stimulation of insulin secretion (GSIS). The remaining portions of unencapsulated (group 3) and encapsulated (group 4) were then frozen for 1–3 days at −80° C. using standard techniques. After thawing, GSIS was also tested in these two groups of islets, using a perifusion model.

GSIS in groups 1, 2 and 3 were comparable, averaging a 2-fold stimulation ($p<0.05$) within 10 minutes of raising the glucose concentration from 3.3 mM (60 mg/dL) to 16.7 mM (300 mg/dL). In group 4, a mean ±SEM of 14.5±0.3% of the capsules were broken after thawing and glucose-stimulated insulin secretion was not observed.

These studies indicate that isolated islets should be cryopreserved unencapsulated and then microencapsulated just prior to use in transplantation.

EXAMPLE 4

Culture of Microencapsulated Islet Cells

The present inventors further studied the effects of culture on microencapsulated islet function. The response to glucose of freshly prepared encapsulated islets (non-cultured microcapsules) was compared to that of cultured encapsulated islets, using a validated in vitro perifision system.

Isolated rat islets were purified by handpicking under a stereomicroscope, and then microencapsulated in alginate-polylysine-alginate using a syringe-air-droplet generator, prior to chelation of the inner alginate core. The encapsulated islets were either tested immediately (control) or cultured for 24 hours prior to perifusion with different concentrations of glucose.

In control (non-cultured) islet microcapsules, the mean±SEM rate of insulin secretion increased from a basal level of 815±5 to 1668±75 pg/6 islets/minute ($p<0.001$, n=5) within ten minutes of raising the glucose concentration from 60 mg/dL (basal) to 16.7 mM (300 mg/dL).

In cultured islet microcapsules, the mean±SEM rate of insulin secretion increased from a basal of 928±46 to 2433±200 pg/6 islets/minute ($p<0.001$, n=7).

The degree of stimulation in the cultured microcapsules (262±20% of basal, $p<0.05$) was greater than that in control (non-cultured) microcapsules (205±9% of basal). These studies indicate that primary culture of encapsulated islet cells enhances their function.

EXAMPLE 5

Transplantation of Microencapsulated Islet Cells

In an anesthetized pig, the pancreas is perifused with University of Wisconsin Solution (DuPont) and pancreatectomy without uncination is performed. The pancreatic ducts are distended with HBSS containing 1 mM Trolox (an antioxidant), 1.5 mg/ml collagenase and 10,000 units DNAse 1. The distended pancreas is placed on ice and digested for 30 minutes, then the pancreas with digestion medium is incubated at 37° C. for twenty minutes prior to shaking by hand for one minute. Digested tissue is then filtered through mesh, then washed in RPMI 1640 with low speed centrifugation. The islet cells are separated on a Ficoll gradient with a COBE automatic cell separator. The isolated naked islet cells are then incubated overnight (18–24 hours) in RPMI 1640 culture media containing at least one each of an antibiotic, antioxidant, anticytokine, and antiendotoxin. A representative medium contains 5 cc of a mixture of streptomycin/penicillin (per 100 ml culture medium), 10 mM dimethylthiourea, 5 mM citiolone, 2 mM L-NMMA, and 10 mM GSH The naked (unencapsulated) islet cells are then cryopreserved (frozen at a minimum temperature of −80° C.) in an antioxidant/cryopreservation cocktail, consisting of medium 199, 2M dimethylsulfoxide, 10% pig serum, 0.7 mM L-glutamine, and 25 mM HEPES.

The frozen islets are then subjected to rapid thawing at 37° C., placed in Kelco's alginate (1000 islets/ml). Kelco's alginate contains 1.4% sodium alginate, 25 mM HEPES, 118 mM NaCl, 2.5 mM MgCl2, at pH=7.4. The alginate is then placed in a syringe and, using a droplet generator, droplets are produced that fall into a funnel filled with calcium solution (1.1% CaCl2, 10 mM HEPES, pH=7.4) to gel the droplets.

The gelled droplets are then washed in saline, incubated in 0.05% Poly-L-Lysine for six minutes, saline washed, incubated in sodium alginate (0.06%) for four minutes, saline washed twice, incubated in 50 mM sodium citrate for seven minutes, and saline washed twice to produce chelated microencapsulated islet cells of 400–700 μM in diameter.

The chelated microencapsulated islet cells are cultured for 3–24 hours in a cocktail containing five ingredients: 10 Mm dimethylurea, 5 mM citiolone, 2 mM N-monomethyl-L-arginine; 10 mM GSH; 5 mM L-glutamine.

Animal subjects (baboons) are rendered diabetic by partial (70%) pancreatectomy and intravenous administration of streptozotocin (65 mg/kg), and are treated with 20 mg/ml 4-methylprednisone (antiendotoxin). Microcapsules are injected intraperitoneally; from about 5,000 to about 15,000 encapsulated islets/kg body weight.

After transplantation, the animals' blood glucose levels are monitored daily.

EXAMPLE 6

Microencapsulation with Sulfate Step

Alginate is an anionic polysaccharide composed of variable homopolymeric regions of mannuronic acid and guluronic acid interspaced with regions of alternating blocks (Smidsrod et al., Trends in Biotechnol. 8: 71–78 (1990)). Cross-linking with divalent cations such as $Ba^{++}$ and $Ca^{++}$ occurs between the carboxyl groups of the guluronic and mannuronic acid chains. However, some of the carboxyl groups remain free even after the cross-linking procedure. This situation allows for unbound positively charged divalent cations to attach to the remaining free negatively charged carboxyl groups within the alginate bead matrix. Also, negatively charged molecules from the HEPES buffer used in the cross-linking step may be entrapped in the alginate beads during the process of cross-linking and the molecules may also bind divalent cations. Therefore, such events produce an undesirable excess of divalent cations being associated with the alginate matrix. The cations are likely undesirable in that they attract water molecules and therefore cause the formation of colloid osmotic pressure. The effect will likely result in weakness, swelling, and possible rupture in such microcapsules.

Figure 5:
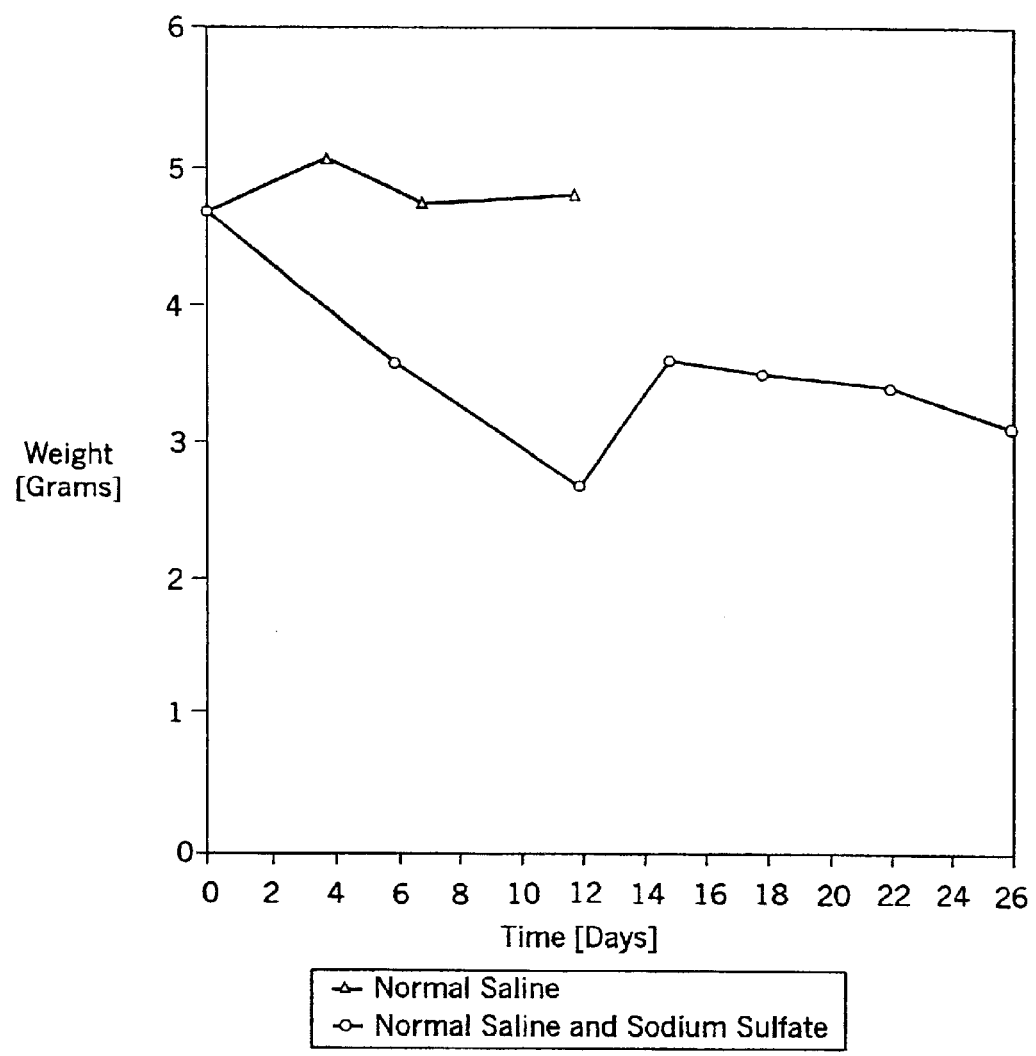
FIG. 5 shows the capsule weight in grams over time in days of control microcapsules and microcapsules treated with sodium sulfate to enhance the durability thereof. The lack of weigh gain over time for the treated microcapsules indicates that stability of such microcapsules.
Figure 6:
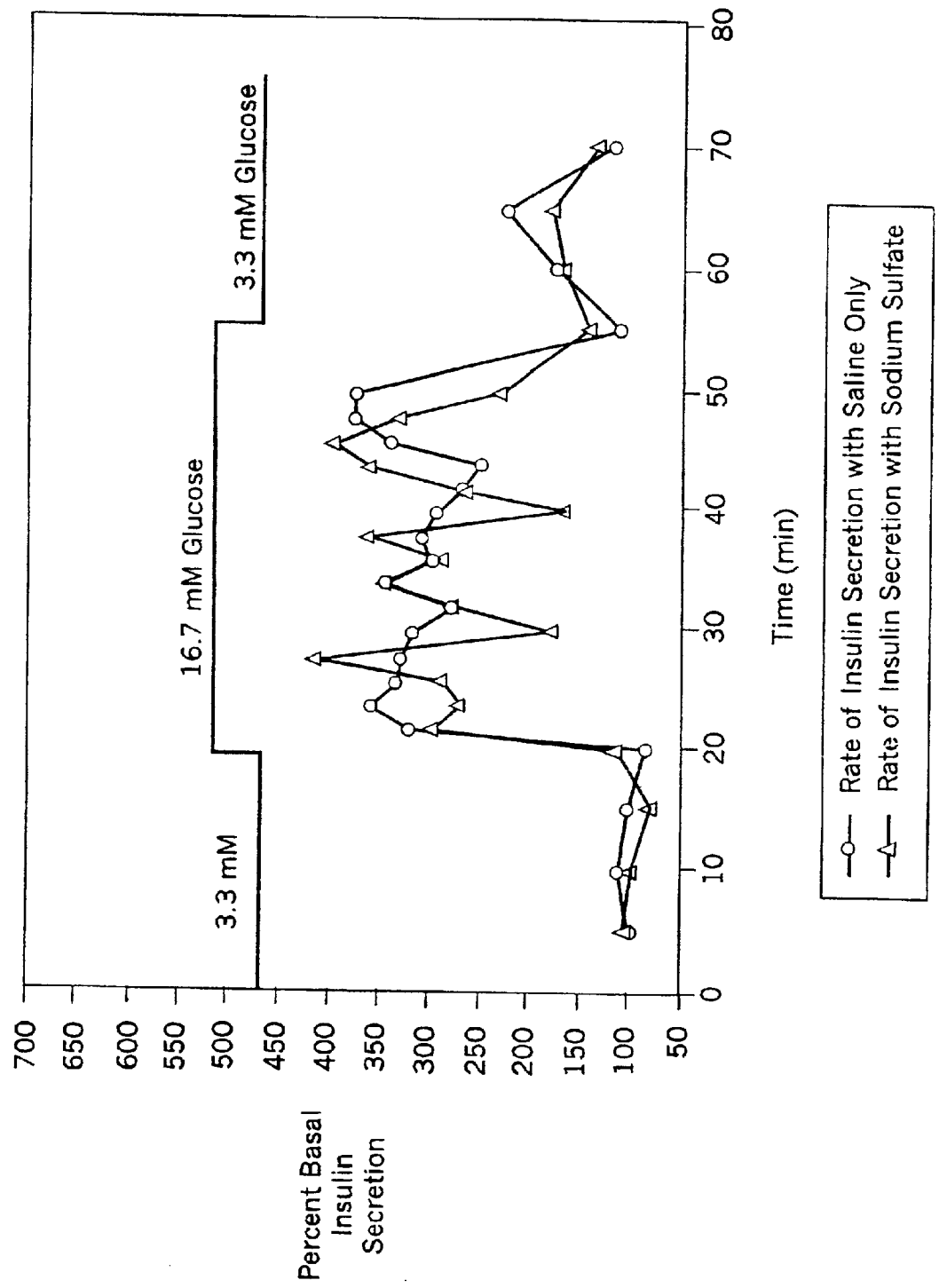
FIG. 6 is a comparison of the percent basal insulin secretion of control and sodium sulfate treated islet capsules. Note that sodium sulfate treated cells exhibited substantially the same responsiveness as the control cells, indicating that the sodium sulfate treatment step used to enhance the durability or stability of the microcapsules was not unduly deleterious to the cells encapsulated therein.

To prevent the possibility of this phenomenon of alginate microcapsule weakness, swelling, and rupture, the alginate beads are washed with sodium sulphate, to induce a chemical reaction designed to eliminate the divalent cation problem, as described above. It was discovered that the incubation of chelated and saline-washed islet microcapsules, as described in previous examples above, in 6 mM sodium sulfate for 30 minutes at room temperature, followed by washing in normal saline (so that excess divalent cations are bound by the sulphate anion), and then culturing at 37 degrees Celsius, results in a significant enhancement of durability (see FIG. 5). Islets contained in the sulfate treated, and more durable microcapsules, are as functionally viable, with regard to their physiological profiles, as those in microcapsules not treated with the sulfate wash step (see FIG. 6).

The foregoing is illustrative of the present invention, and is not to be construed as limiting thereof. The invention is defined by the following claims, with equivalents of the claims to be included therein.

I claim:

1. A microencapsulated islet cell product comprising microcapsules containing isolated living pancreatic islet cells therein, said microcencapsulated islet cells exhibiting a weight gain of not more than 10 percent by weight over a period of one month in physiological saline solution at 37 degrees Celsius and exhibiting at least 150 percent basal insulin secretion in response to 16.7 milliMolar glucose challenge in Krebs-Ringer physiological solution at pH 7.4 after said period of one month.

2. A product according to claim 1, where said microcapsule comprises a polysaccharide gum surrounded by a semipermeable membrane.

3. A product according to claim 1, where said microcapsule comprises alginate in combination with polylysine, polyornithine, and combinations thereof.

4. A product according to claim 1, wherein said microcapsule has an internal cell-containing core of alginate.

5. A product according to claim 4 wherein said internal cell-containing core of alginate is gelled.

6. A product according to claim 1, wherein said internal cell-containing core of alginate is not gelled.

7. A product according to claim 1, wherein said microcapsule has a diameter of from about 50 $\mu$m to about 2 mm.

8. A product according to claim 1, wherein said microcapsule has a diameter of from about 200 $\mu$m to about 1000 $\mu$m.

9. A product according to claim 1, wherein said microcapsule has a diameter of from about 300 $\mu$m to about 700 $\mu$m.

10. A microencapsulated islet cell product according to claim 1, wherein said microencapsulated islet cell is produced by the process of incubating said microcapsule following microencapsulation with a physiologically acceptable salt to increase the durability of the microcapsule.

11. A microencapsulated islet cell product comprising microcapsules containing isolated living pancreatic islet cells therein, said microcencapsulated islet cells exhibiting a weight gain of not more than 10 percent by weight over a period of one month in physiological saline solution at 37 degrees Celsius and exhibiting at least 150 percent basal insulin secretion in response to 16.7 milliMolar glucose challenge in Krebs-Ringer physiological solution at pH 7.4 after said period of one month;

wherein said microcapsule comprises a polysaccharide gum surrounded by a semipermeable membrane;

and wherein said microcapsule has a diameter of from about 300 $\mu$m to about 700 $\mu$m.

12. A microencapsulated islet cell product according to claim 11, wherein said microencapsulated islet cell is produced by the process of incubating said microcapsule following microencapsulation with a physiologically acceptable salt to increase the durability of the microcapsule.

* * * * *